United States Patent [19]
Suzuki et al.

[11] Patent Number: 5,767,962
[45] Date of Patent: Jun. 16, 1998

[54] INSPECTION SYSTEM AND DEVICE MANUFACTURING METHOD USING THE SAME

[75] Inventors: Masayuki Suzuki, Utsunomiya; Noriyuki Nose, Atsugi; Minoru Yoshii, Tokyo; Kyoichi Miyazaki, Utsunomiya; Toshihiko Tsuji, Utsunomiya; Seiji Takeuchi, Utsunomiya, all of Japan

[73] Assignee: Canon Kabushiki Kaisha, Tokyo, Japan

[21] Appl. No.: 755,352

[22] Filed: Nov. 25, 1996

Related U.S. Application Data

[63] Continuation of Ser. No. 370,615, Jan. 10, 1995, abandoned.

[30] Foreign Application Priority Data

Jan. 13, 1994 [JP] Japan ................................. 6-014897

[51] Int. Cl.⁶ .................................................. G01N 21/00
[52] U.S. Cl. ........................... 356/237; 359/205; 356/239
[58] Field of Search ................................... 356/237, 239, 356/394, 429–431; 250/561, 563, 572; 359/205–219

[56] References Cited

U.S. PATENT DOCUMENTS

| | | | |
|---|---|---|---|
| 4,676,637 | 6/1987 | Uto et al. | 356/237 |
| 4,795,911 | 1/1989 | Kohno et al. | 250/572 |
| 4,966,457 | 10/1990 | Hayano et al. | 356/239 |
| 5,105,092 | 4/1992 | Natsubori et al. | 250/572 |
| 5,270,794 | 12/1993 | Tsuji et al. | 356/371 |
| 5,369,486 | 11/1994 | Matsumoto et al. | 356/349 |

FOREIGN PATENT DOCUMENTS 04 143640  5/1992  Japan.

*Primary Examiner*—Hoa Q. Pham
*Attorney, Agent, or Firm*—Fitzpatrick, Cella, Harper & Scinto

[57] ABSTRACT

An inspection system includes a light source, a scanning device for scanning a surface to be inspected, with light from the light source, wherein the scanning device includes an optical member disposed with inclination with respect to a primary scan direction, the optical member being adapted to provide a convergent light being converged to form a spot at a distance changeable with the position of a scan, and a light receiving device for receiving scattered light from the surface.

7 Claims, 14 Drawing Sheets

F I G. I

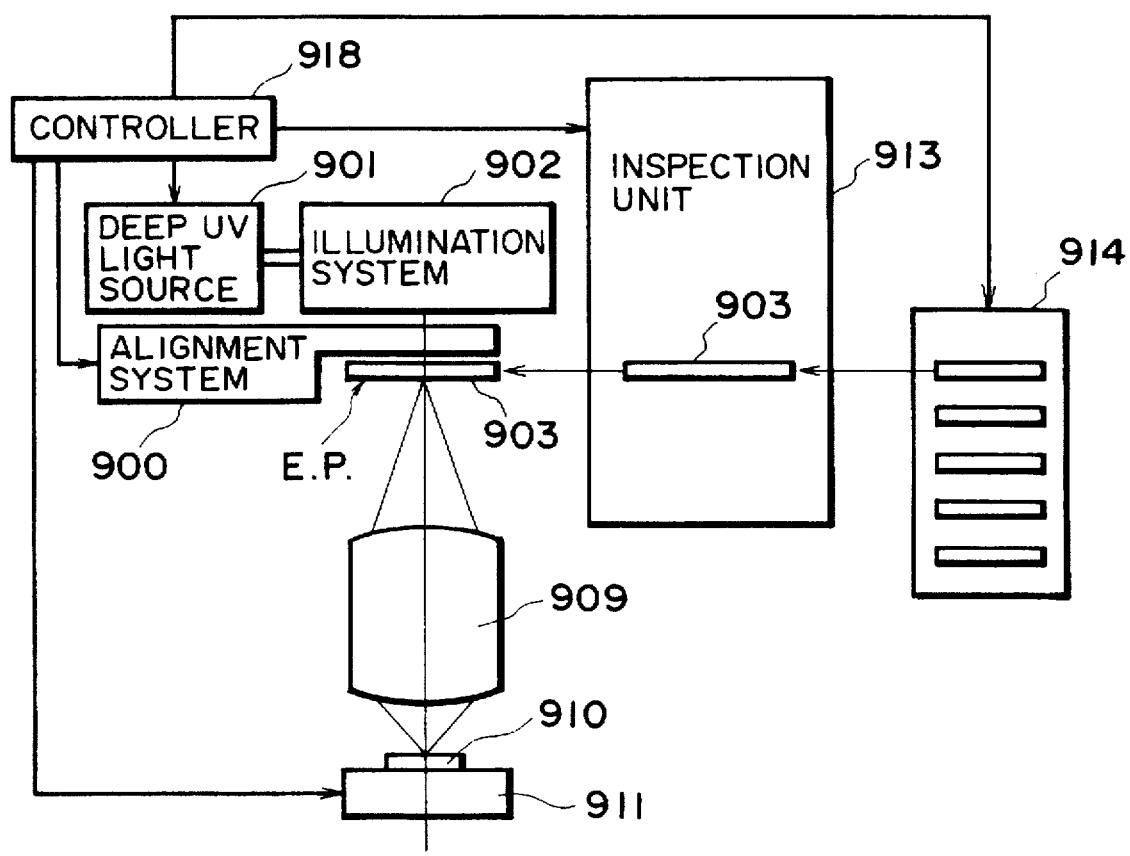
F I G. 14

INSPECTION SYSTEM AND DEVICE MANUFACTURING METHOD USING THE SAME

This application is a continuation of application Ser. No. 08/370,615, filed Jan. 10, 1995, now abandoned.

FIELD OF THE INVENTION AND RELATED ART

This invention relates to an inspection system and a device manufacturing method using the same. More particularly, the invention is suitably usable in a semiconductor device manufacturing apparatus, for example, for detecting with good precision the presence or absence of a foreign particle such as non-transparent dust or the like or the position of the same, on or adhered to the surface of an original such as a reticle, having a circuit pattern, or the surface of a pellicle protection film mounted to the original.

Generally in IC manufacturing processes, a circuit pattern formed on an original such as a reticle or photomask is transferred to the surface of a wafer, coated with the a resist, with use of a semiconductor printing apparatus such as a stepper or a mask aligner.

In such a lithographic process, if a foreign particle such as dust or any fault of a pattern is present on the surface of the original, such a particle is transferred to the wafer together with the circuit pattern, and this leads to reduced yield of IC manufacture.

For this reason, in the IC manufacturing processes, it is required to inspect the presence of such foreign particle on a substrate. Thus, many proposals have been made in this respect.

In many cases, an inspection method based on the phenomenon of isotropic scattering of light from a particle is employed. FIGS. 16 and 17 show an example, wherein FIG. 16 is a schematic view of a main portion of a particle inspection system for inspecting the presence or absence of a particle on the basis of detection of scattered light from the particle, and FIG. 17 is a plan view of the main portion.

In these drawings, a laser beam from a laser light source 151 is transformed by a collimator system 152, for example, into a beam best suited to the particle inspection. It is then directed to a scanning optical system which comprises a scanning mirror 153, such as a polygonal mirror being rotatable about a rotational axis 153a in the direction of an arrow 153b, and a lens system 154 such as an f-θ lens, for example. The scanning laser beam from the lens system 154 is collected onto the surface 155 to be inspected, as a scanning spot 156. This surface corresponds to a reticle, for example, on which a circuit pattern is provided. A scanning stage system, not shown, relatively moves the surface 155 in a direction 158 perpendicular to the scan direction 157 of the scanning spot 156, by which the surface 155 as a whole can be inspected.

A detection system 163 comprising a lens system 159, an aperture 160 and a photodetector 161, is disposed backwardly or sidewardly with respect to the direction of projection of this laser beam. Such placement of the detection system 163 is adopted because: the scattered light produced from a circuit pattern, for example, in response to impingement of the laser beam upon the surface 155 to be inspected has a particular polarization direction or directions, so that the detection system is disposed so as not to receive such light.

With such a structure, if there is no particle within the scan spot 156, no scattered light is detected by the photodetector 161. If there is a particle, scattered light is produced isotropically from the small particle such that the photodetector 161 detects scattered light. A detection signal produced thereby is processed by a signal processing system 162, and inspection of the presence or absence of a particle is performed.

FIG. 18 is a schematic view of a main portion of a particle inspection system of the type disclosed in Japanese Laid-Open Patent Application, Laid-Open No. 143640/1992.

In the drawing, a laser beam from a laser light source 171 is directed through a filter 172 and a lens system 173, and it is collected onto a swingable mirror 174. The laser beam from the swingable mirror 174 is transformed by a scanning lens system 175 into a parallel beam by which the surface 176 to be inspected is scanned in the direction of an arrow 177. Here, with such an optical scan, the surface 176 to be inspected is moved in the direction perpendicular to the sheet of the drawing, such that the entirety of the surface 176 is scanned. Thus, the surface 176 as a whole can be inspected. Scattered light from the surface 176 being inspected is collected by a condensing lens 178 onto the surface of a photodetector 178, and the presence or absence of a particle upon the surface 176 is detected on the basis of an output signal of the photodetector 178.

SUMMARY OF THE INVENTION

In the particle inspection system of FIGS. 16 and 17, there is a relative inclination between the detection surface of the detecting system 163 and the surface 155 to be inspected. This causes a problem that, if the position of the laser beam in the primary scan direction 157 changes, the numerical number (N.A.) of the detection system 163 changes, resulting in that the detection sensitivity changes with the scan position.

Also, in the particle inspection system of FIG. 18, the projected light from the scanning optical system 175 comprises parallel light and, therefore, the spot diameter on the surface 176 being inspected becomes relatively large. This causes a difficulty in detecting the presence or absence of a minute particle.

It is accordingly an object of the present invention to provide an inspection system for detecting the presence or absence of a particle on a surface to be inspected or the position of such a particle very precisely, this being assured by suitably setting the condition of scanning of the surface with light or the structure of a scanning lens system.

It is another object of the present invention to provide a device manufacturing method which is based on a particle inspection system such as described above.

In accordance with an aspect of the present invention, there is provided an inspection system, comprising: a light source; scanning means for scanning a surface to be inspected, with light from said light source, said scanning means including an optical member disposed with inclination with respect to a primary scan direction, said optical member being adapted to provide a convergent light being converged to form a spot at a distance changeable with the position of scan; and light receiving means for receiving scattered light from the surface.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 14 is a block diagram of a main portion of a semiconductor device manufacturing method according to an embodiment of the present invention.

DESCRIPTION OF THE PREFERRED EMBODIMENTS

[First Embodiment]

Figure 1:
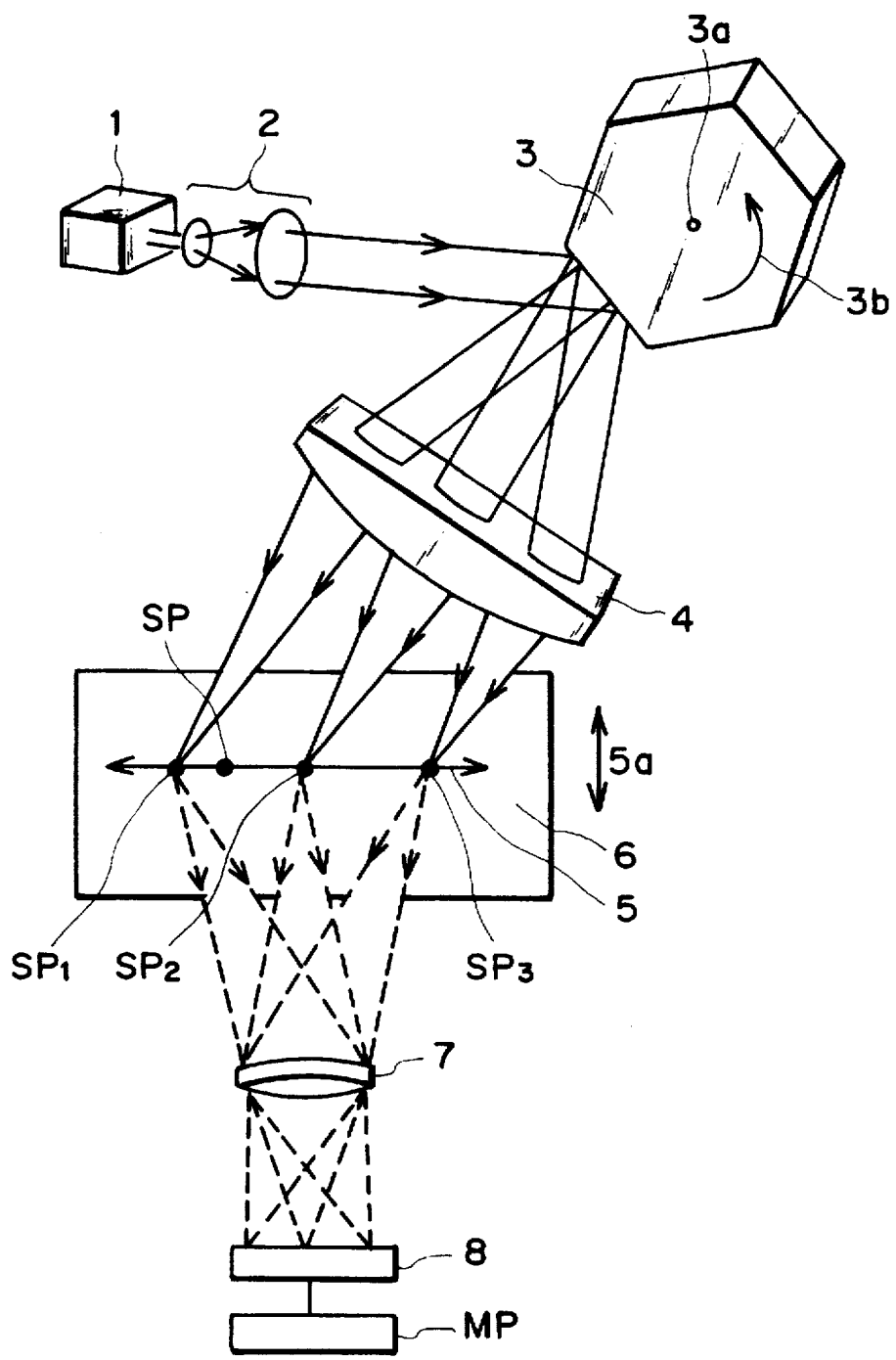
FIG. 1 is a schematic view of a main portion of a first embodiment of the present invention.
Figure 2:
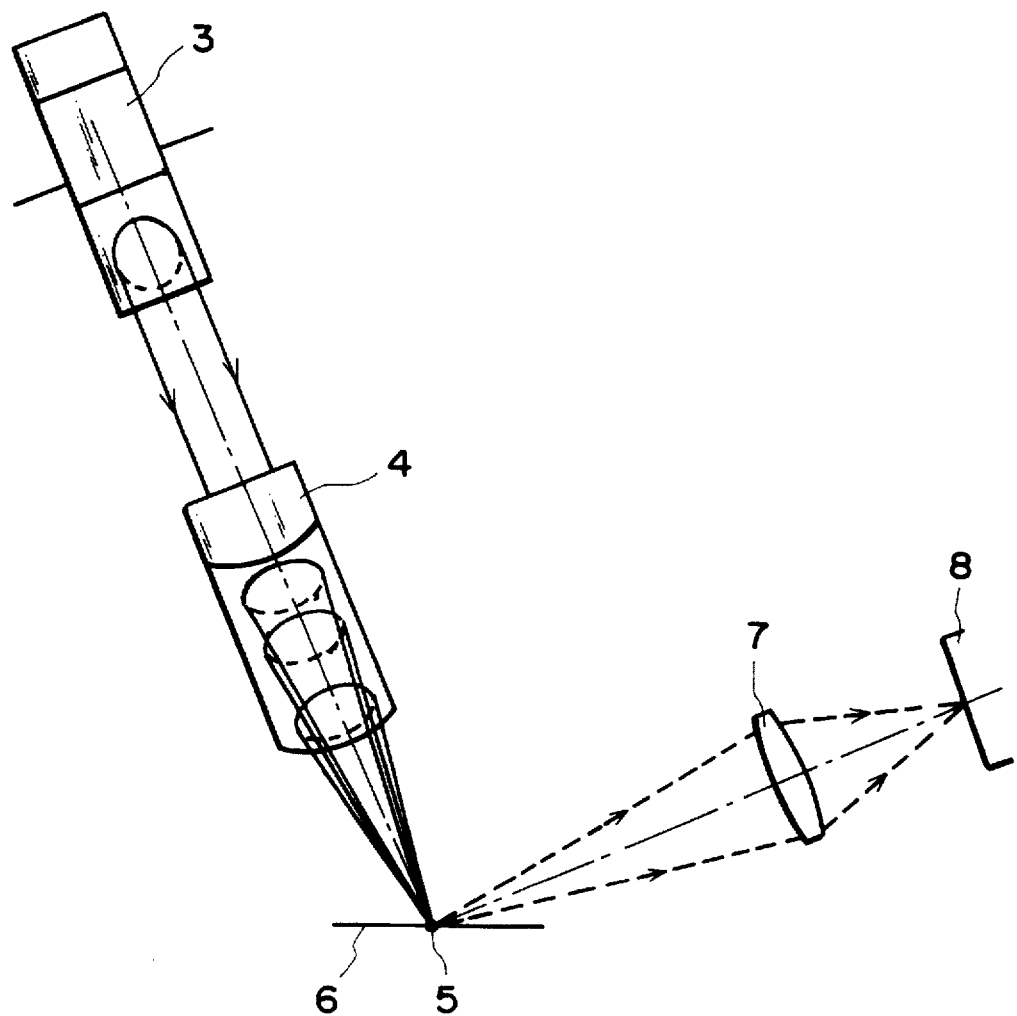
FIG. 2 is a sectional view of a main portion of the first embodiment of the present invention.

FIG. 1 is a schematic view of a main portion of a first embodiment of the present invention, and FIG. 2 is a sectional view of a portion of FIG. 1.

In this embodiment, the invention is applied to an inspection system for inspecting the state of a surface to be inspected, such as a surface of an exposure original (reticle or photomask) used in the field of semiconductors, or a surface of a wafer, and more specifically, for inspecting the presence or absence of a foreign particle such as dust adhered to the surface to be inspected or a fault such as a scratch, for example, on the surface to be inspected. Hereinafter, such a foreign particle or a fault will be referred to simply as a "particle".

It is to be noted that this embodiment is applicable not only to an inspection system to be used in the field of semiconductors, but also it is applicable widely to an inspection system for inspecting the state of a surface to be examined.

In FIG. 1, denoted at 1 is a light source, and it comprises a laser, for example. Denoted at 2 is a beam expander for expanding the beam diameter of a laser beam from the light source 1, and it emits parallel light. Denoted at 3 is a polygonal mirror (rotatable polyhedron mirror) which is rotatable about a rotational axis 3a in the direction of an arrow 3b at a constant rotational speed to reflectively deflect the light from the beam expander 2. Denoted at 4 is a scanning lens system for collecting the light from the polygonal mirror 3 to form a spot SP upon a surface 6 to be inspected, such as an original.

By rotating the polygonal mirror 3 with a motor (not shown), for example, the surface 6 to be inspected can be optically scanned with the spot SP in the primary scan direction 5. The polygonal mirror 3 and the scanning lens system 4 are components of a scanning system.

Denoted at 7 is a light receiving lens. If there is a particle on the surface (original) 6 to be inspected, in response to irradiation thereof with the spot light SP, reflectively scattered light is produced therefrom. The thus produced reflectively scattered light is collected by the light receiving lens 7 toward a photodetector 8. The photodetector 8 then serves to photoelectrically convert the received scattered light. The light receiving lens 7 and the photodetector 8 are components of a detecting means. Denoted at MP is signal processing means which serves to discriminate the presence or absence of a particle on the surface 6 being inspected, on the basis of an output signal of the photodetector 8, for example, on the basis of the intensity of the output signal.

As shown in FIG. 1, the scanning lens system 4 of this embodiment is opposed to the surface 6 to be inspected and inclined with respect to the primary scan direction 5. The distances from the scanning lens system 4 to the spot positions SP1, SP2 and SP3 on the surface 6 along the primary scan direction 5, are different from each other. Thus, the scanning lens system 4 has a lens portion having a rotationally asymmetrical refracting power such that light spots SP can be imaged at different positions on the surface 6 along the primary scan direction 5 which positions are at different distances from the scanning lens system 4. Namely, the scanning lens system 4 of this embodiment comprises a lens system having a refracting power and/or a principal point on an image side which changes with the picture angle, and it has a lens shape by which the spot imaging position changes with the picture angle.

In this embodiment, the polygonal mirror 3 is rotated so that the surface 6 to be inspected is optically scanned in the primary scan direction 5 and, additionally, the surface 6 is moved in the direction (secondary scan direction) denoted by an arrow 5a, by which the whole of the surface 6 is optically scanned. In this manner, inspection of the presence or absence of any particle is made to the entirety of the surface 6.

Details of the structure of the scanning lens system 4 of this embodiment will be explained below.

FIGS. 3–6 are sectional views each of a lens portion of the scanning lens system 4 of the present embodiment.

Figure 3:
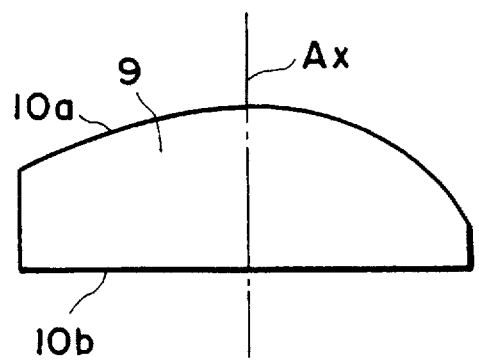
FIG. 3 is a schematic view for explaining a scanning lens system of FIG. 1.

In the lens portion 9 shown in FIG. 3, denoted at 10a is a lens surface having a continuously changing curvature. Lens surface 10b is flat. In this drawing, denoted at Ax is an optical axis. Within the plane of the sheet of the drawing, the lens surface 10a is asymmetric with respect to the optical axis Ax. Within a plane perpendicular to the sheet of the drawing, it is symmetric with respect to the optical axis Ax. The lens surface 10b has an uneven refracting power which becomes smaller toward the left of the lens and becomes larger toward the right of the lens as viewed in the drawing. In each position, the refracting power is positive.

Figure 4:
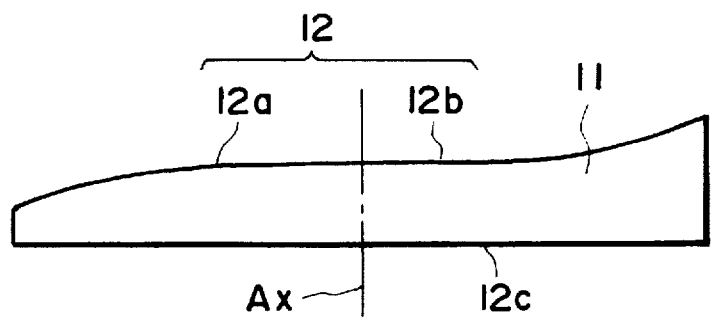
FIG. 4 is a schematic view for explaining a scanning lens system of FIG. 1.

In the lens portion 11 shown in FIG. 4, denoted at 12 is a lens surface changing continuously. Within the plane of the sheet of the drawing, it is asymmetric with respect to the optical axis Ax. Within a plane perpendicular to the sheet of the drawing, it is symmetric with respect to the optical axis Ax. The lens surface 12 has an uneven refracting power whose absolute value increases continuously with increasing distance from the optical axis. At the left side of the optical axis Ax, the lens surface 12 has a positive refracting power and, at the right side of the optical axis Ax, it has a negative refracting power. Lens surface 12c is flat. As the scanning lens system, the lens portion 11 may be used in combination with a spherical lens, for example, having a positive refracting power.

Figure 5:
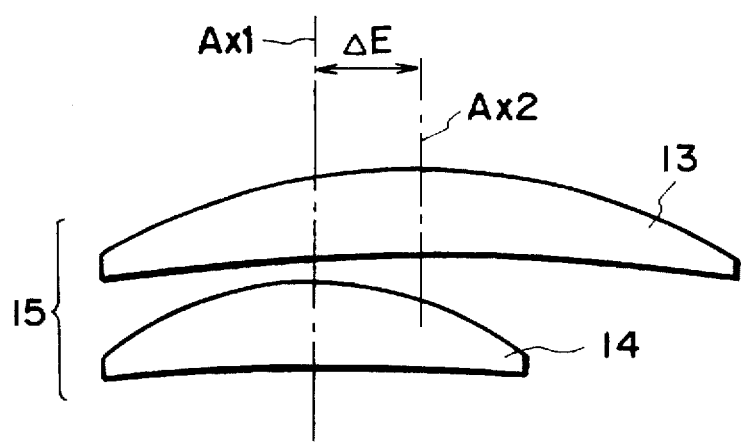
FIG. 5 is a schematic view for explaining a scanning lens system of FIG. 1.

The lens portion 15 shown in FIG. 5 has a lens structure wherein a spherical lens 14 having an optical axis Ax1 and another spherical lens 13 having an optical axis Ax2 are used in combination, with their optical axes being disposed with a mutual parallel shift ΔE.

Figure 6:
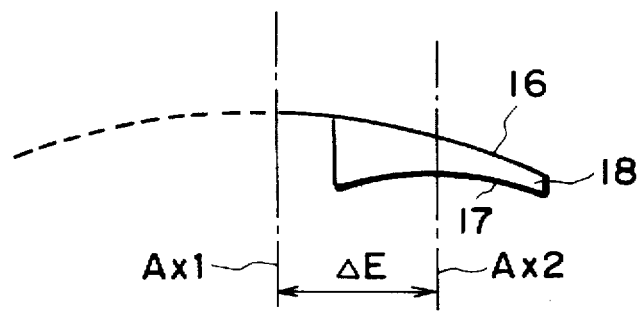
FIG. 6 is a schematic view for explaining a scanning lens system of FIG. 1.

The lens portion 18 shown in FIG. 6 has a lens shape that a lens surface 16 is spherical (convex) and has an optical axis Ax1 while a lens surface 17 is spherical (concave) and has an optical axis Ax2, with their spherical surfaces being parallel shifted by ΔE.

The lens portions shown in FIGS. 3–6 each is a component of the scanning lens system of the present embodiment.

[Second embodiment]

Figure 7:
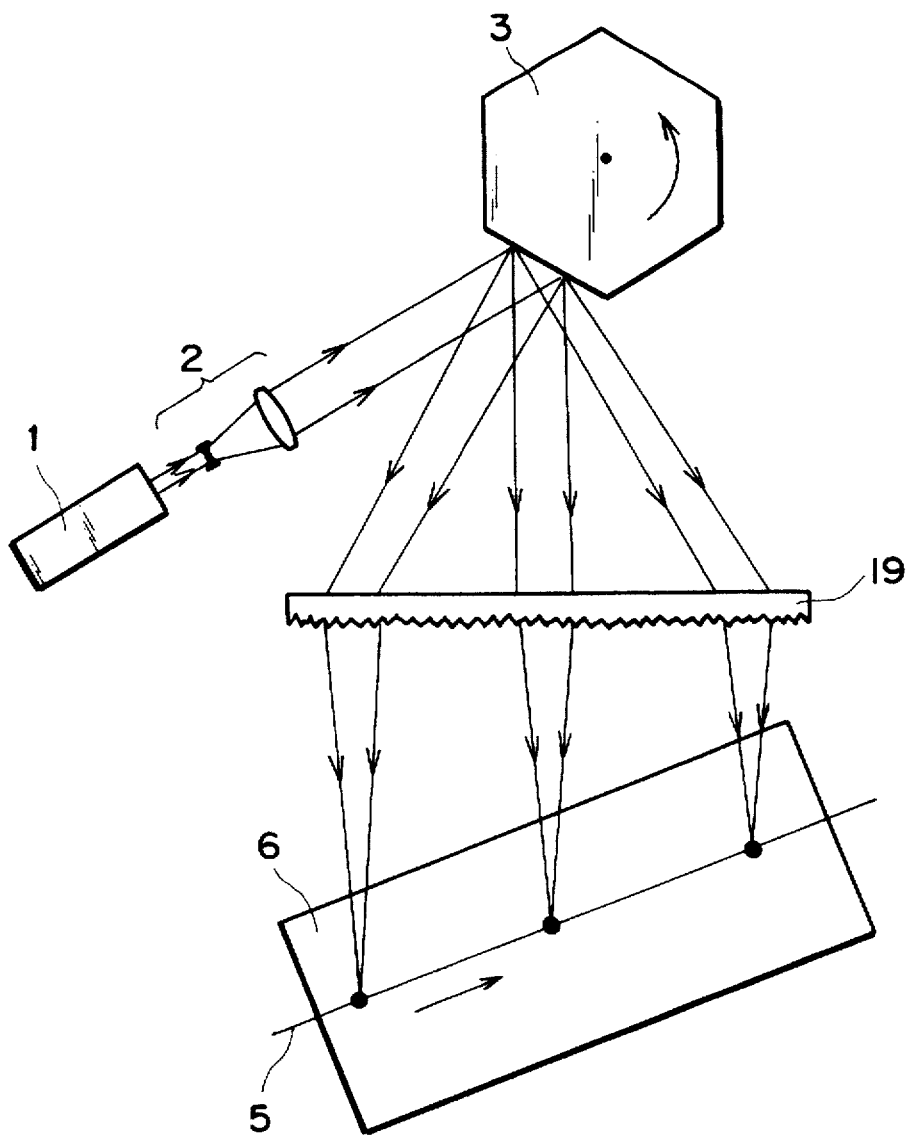
FIG. 7 is a schematic view of a main portion of a second embodiment of the present invention.

FIG. 7 shows a second embodiment which differs from the first embodiment of FIG. 1 in that: it uses a hologram device 19 having an imaging function, as an optical member of a scanning lens system. The condition of scan with the use of a laser beam and the like are essentially the same as that of the preceding embodiment. The hologram device 19 may be so arranged to provide a changing focal length, this being able to be done by, for example, changing the grating pitch with position. Thus, the point of convergence changes with the incidence position or incidence angle of light.

Substantially the same optical performance as that of the scanning lens system 4 of the first embodiment is thus provided. As for the hologram device, a reflection type one may be applicable similarly, as a transmission type one. Also, the hologram device may be equipped with a function for separating a spot and a zeroth order diffraction light in the secondary scan direction, so as to avoid overlapping of them upon the surface 6 being inspected.

[Third embodiment]

Figure 8:
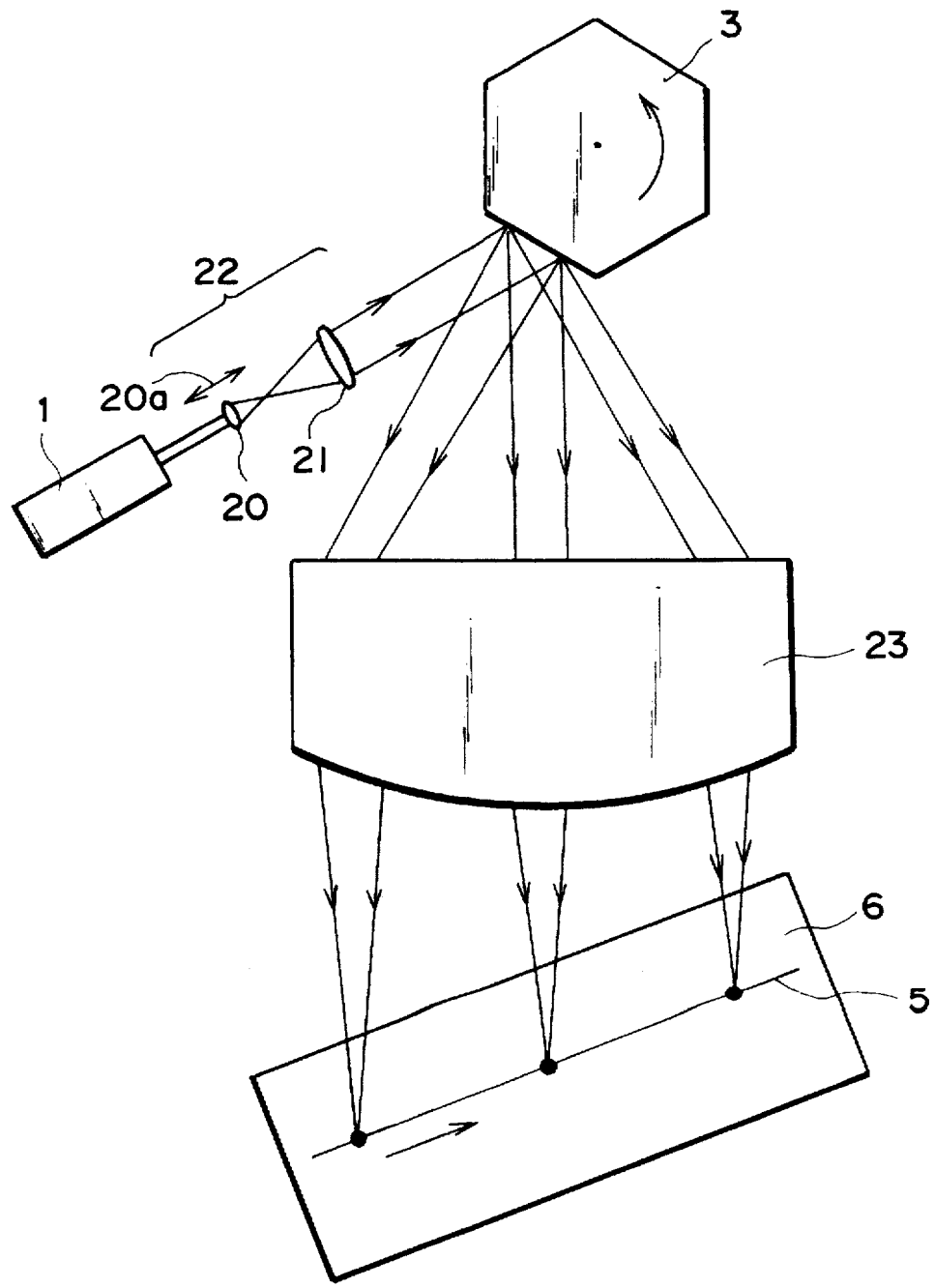
FIG. 8 is a schematic view of a main portion of a third embodiment of the present invention.

FIG. 8 shows a third embodiment which differs from the first embodiment of FIG. 1 in that: a lens system 23 (focal length f3) having a spherical surface which, within the plane of scan, is symmetrical with respect to an optical axis, is used as a scanning lens system, and that, in place thereof, one (20) of lenses constituting a beam expander 22 is moved oscillatingly along the optical axis direction (arrow 20a) in timed relation with the scan, to thereby produce light spots at different positions (distances) on the surface 6 to be inspected. The structure of the remaining portion of this embodiment is essentially the same as that of the first embodiment.

Also in this embodiment, the beam expander 22 comprises a lens 20 having a positive refracting power (focal length f1) and a lens 21 having a positive refracting power (focal length f2). Here, the beam expanding magnification is equal to f2/f1. The displacement Z of the spot in the optical axis direction, upon the surface 6 to be inspected, following the displacement Δx of the lens 20 in the optical axis direction, is given by:

$$Z = (f3/f2)^2 \cdot \Delta x$$

If the lens 20 moves in a direction away from the lens 21, a scan line 5 such as shown in FIG. 8 is defined. In this embodiment, upon completion of one primary scan operation with the laser beam, the lens 20 moves back to its initial position a before start of the next scan operation.

In this embodiment, in place of the lens 20, the lens 21 may be moved oscillatingly along the optical axis direction. Also, the beam expander 22 may comprise a lens of negative refracting power and a lens of positive refracting power, while one of them may be moved along the optical axis.

[Fourth Embodiment]

Figure 9A:
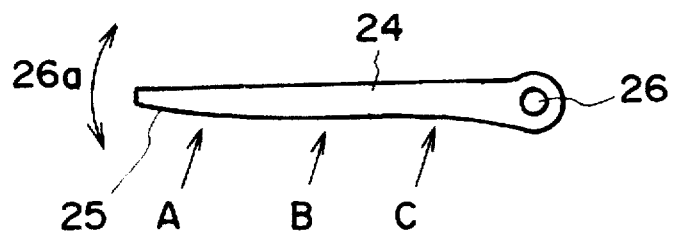
FIGS. 9A and 9B are schematic views each showing a main portion of a fourth embodiment of the present invention.
Figure 9B:
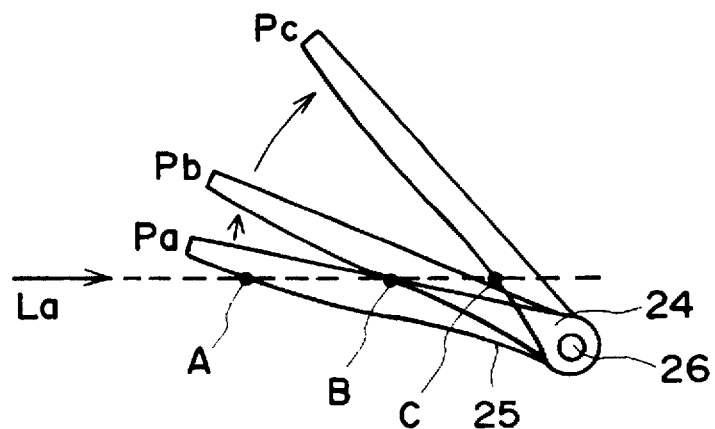

FIGS. 9A and 9B show a fourth embodiment. Denoted at 24 is a deflector (swingable member) for reflectively deflecting a laser beam. This embodiment differs from the first embodiment of FIG. 1 in that: in place of a polygonal mirror, the deflector 24 is used, and that a spherical lens system is used as a scanning lens system. The structure of the remaining portion is essentially the same as that of the first embodiment.

The deflector 24 of this embodiment is made pivotable about a rotational shaft 26, as depicted by an arrow 26a. Reflection surface 25 has a refracting power changing with position. For example, in a region A, it defines a divergent surface of convex shape. In a region B, it defines a flat surface, and in region C, it defines a convergent surface of convex shape.

As best seen in FIG. 9B, the deflector 24 is swingingly moved so that the laser beam La, projected thereto from the left, is reflected in each of the different regions on the reflection surface 25. If, for example, the deflector 24 is at positions Pa, Pb and Pc, respectively, at different moments, the laser beam is reflected by the regions A, B and C of the reflector 24, respectively. In this manner, with the scan angle of the scanning system, the deflector 24 provides a changing refracting power to the input light beam, such that as in the first embodiment light spots are imaged along the primary scan direction on the surface 6 being inspected, from the oblique direction.

[Fifth Embodiment]

Figure 10:
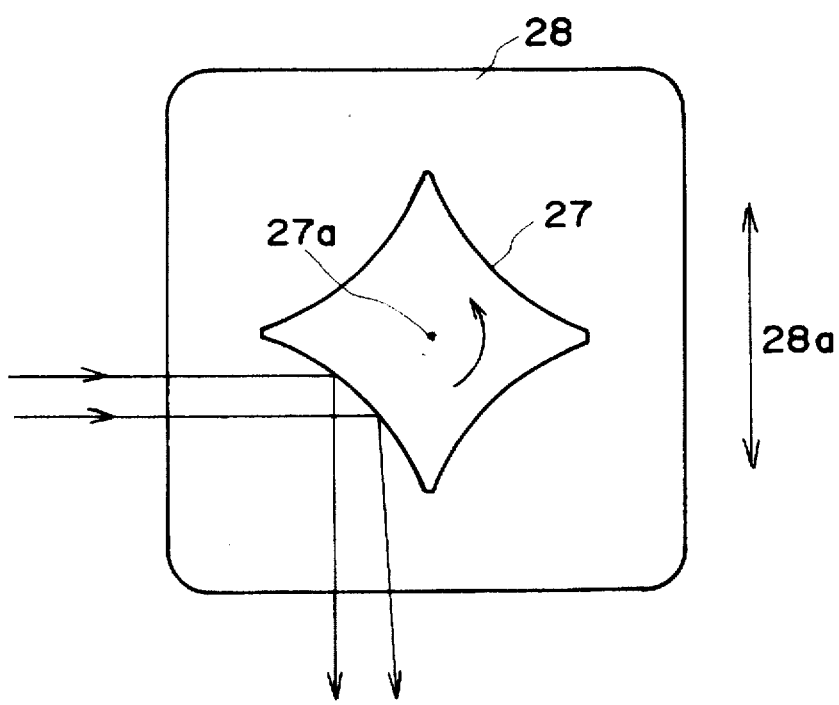
FIG. 10 is a schematic view of a main portion of a fifth embodiment of the present invention.

FIG. 10 shows a fifth embodiment. Denoted at 27 is a rotatably polygonal mirror having cylindrical mirror surfaces each of a concave shape within the plane of scan. Denoted at 28 is a motor for rotating the rotatable polygonal mirror 27 about a rotational axis 27a.

In this embodiment, the rotatable polygonal mirror 27 and the motor 28 are oscillated in the direction of an arrow 28a in timed relation with the scan in the primary scan direction. As a result of this, the object point displaces along the optical axis direction, following a change in picture angle in scan (a change in scan angle), such that as in the first embodiment laser beam spots are imaged along the primary scan direction on the surface 6 being inspected, from the oblique direction.

[Sixth Embodiment]

Figure 11:
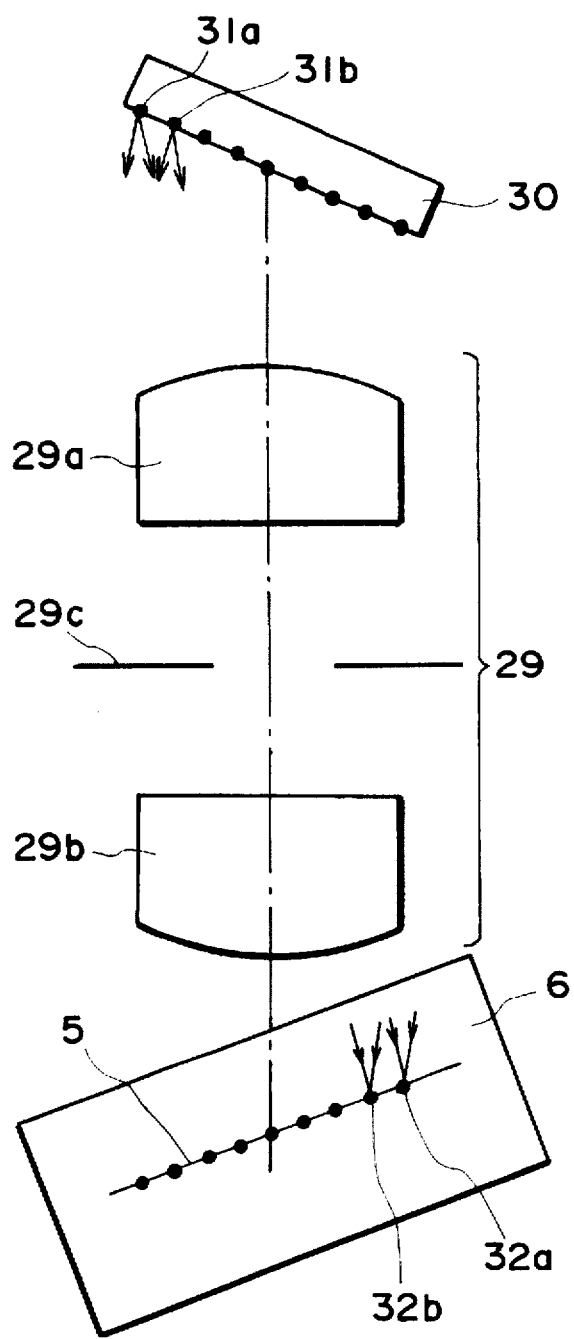
FIG. 11 is a schematic view of a main portion of a sixth embodiment of the present invention.

FIG. 11 is a schematic view of a main portion of a sixth embodiment of the present invention.

In the drawing, denoted at 29 is a projection lens which includes lenses 29a and 29b having rotationally symmetrical lens surfaces. Denoted at 30 is an LED array (light emitting means). Denoted at 31a, 31b, . . . , etc., are light emitting points (light emitting elements) of the LED array 30, respectively. Denoted at 32a, 32b, . . . , etc., are imaging points on a surface 6 to be inspected, corresponding to the light emitting points 31a, 31b, . . . , etc., of the LED array 30. The projection lens 29 comprises a front lens group 29a, a rear lens group 29b and a stop 29c.

In the drawing, the plane containing the light emitting points 31a, 31b, . . . , etc., of the LED array 30 is disposed with inclination with respect to a direction perpendicular to the optical axis of the projection lens 29. Therefore, the image plane is also inclined with respect to a direction perpendicular to the optical axis.

The light spot scan is made by sequentially turning on the light emitting points 31a, 31b, . . . , etc., of the LED array 30. Namely, first, in response to lighting the light emitting point 31a, a spot is formed at the position 32a on the surface 6 to be inspected. Then, the light emitting point 31a is turned off, and the light emitting point 31b is turned on such that a spot is formed at the position 32b on the surface 6 to be inspected. By sequentially turning on and off the light emitting points of the LED array 30 in this manner, the light spot scan of the image plane, that is, the surface 6 to be inspected, is performed. The primary scan direction 5 on the surface 5 to be inspected, by the light spots, is inclined within the plane of scan, with respect to a direction perpendicular to the optical axis of the projection lens 29.

[Seventh Embodiment]

Figure 12:
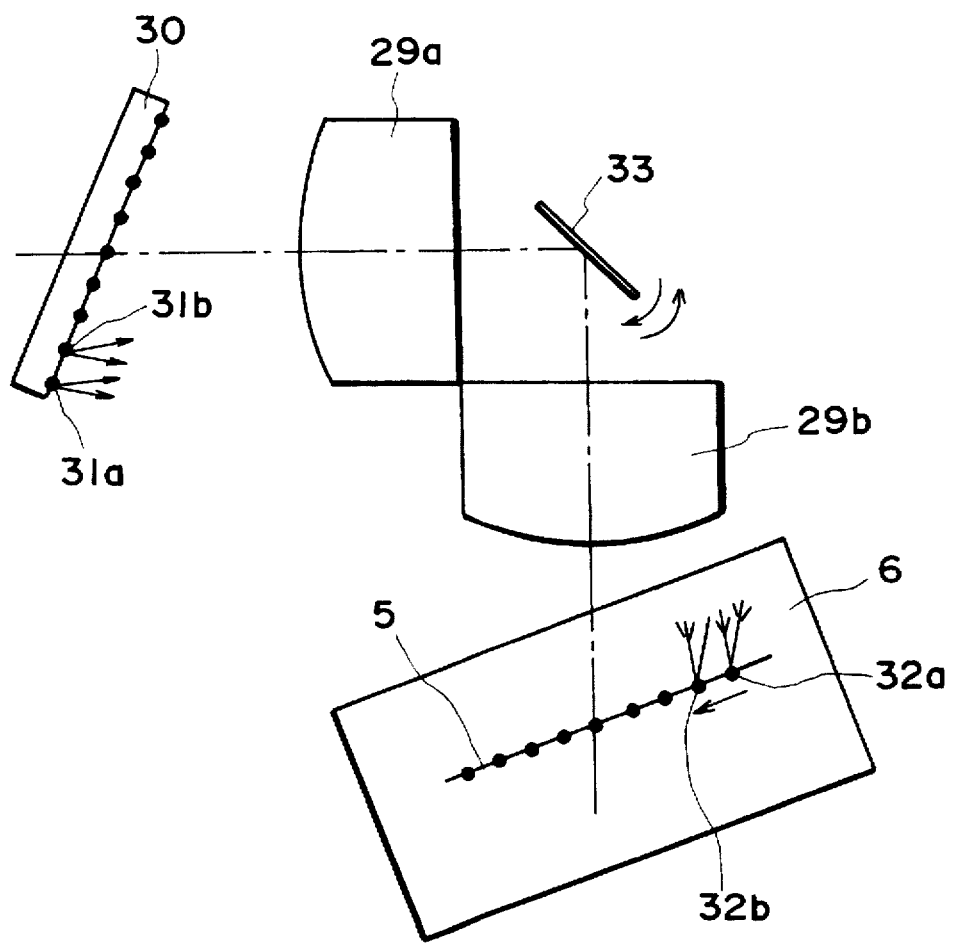
FIG. 12 is a schematic view of a main portion of a seventh embodiment of the present invention.

FIG. 12 is a schematic view of a seventh embodiment of the present invention.

This embodiment differs from the sixth embodiment shown in FIG. 11 in that: a deflector 33 comprising a rotatable mirror is disposed between the front lens group 29a and the rear lens group 29b, the rotatable mirror being rotationally moved in timed relation with the optical scan with light emission of the light emitting points 31a, 31b, . . . , etc., of the LED lens array 30, to thereby continuously optically scan the surface 6 to be inspected. The structure of the remaining portion is essentially the same as that of the sixth embodiment.

More specifically, in the light spot scan of this embodiment, first the light emitting point 31a is turned on by which a light spot is formed at the position 32a. Thereafter, while keeping the light emitting point 31a lighted, the deflector 33 is minutely rotated to scanningly displace the light spot from the position 32a to the position 32b. Then, the light emitting point 31a is turned off, and the deflector 33 is minutely rotated in the reverse direction back to its initial position. Then, the light emitting point 31b is turned on, by which a light spot is formed at the position 32b.

By repeating this operation, upon the image plane (surface 6), a continuous light spot scan in the scan direction 5 is performed. Here, the scan direction 5 is inclined with respect to a direction perpendicular to the optical axis of the lens system 29b.

[Eighth Embodiment]

Figure 13:
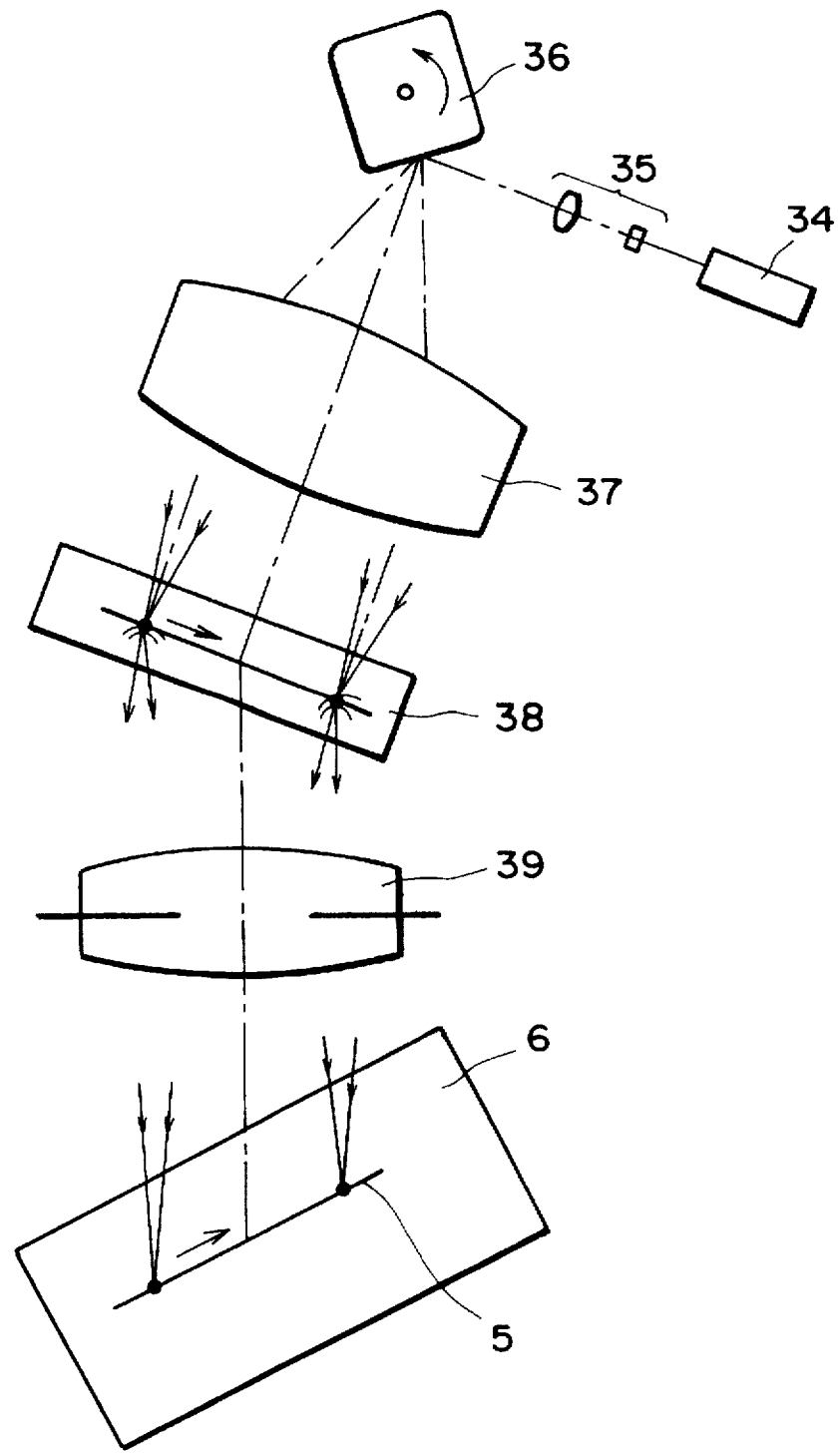
FIG. 13 is a schematic view of a main portion of an eighth embodiment of the present invention.

FIG. 13 is a schematic view of a main portion of an eighth embodiment of the present invention.

Figure 16:
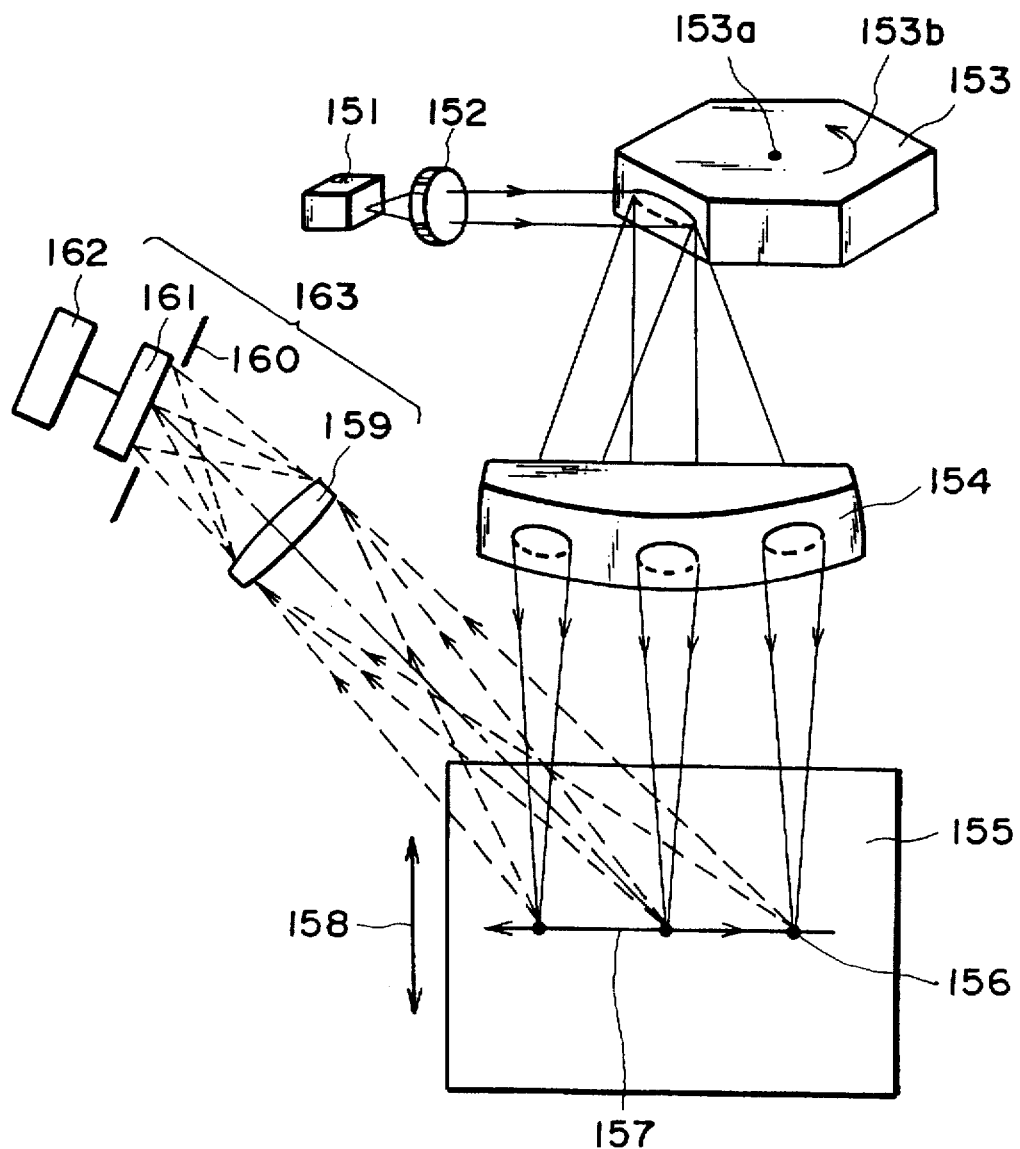
FIG. 16 is a schematic view of a main portion of a known type particle inspection system.
Figure 17:
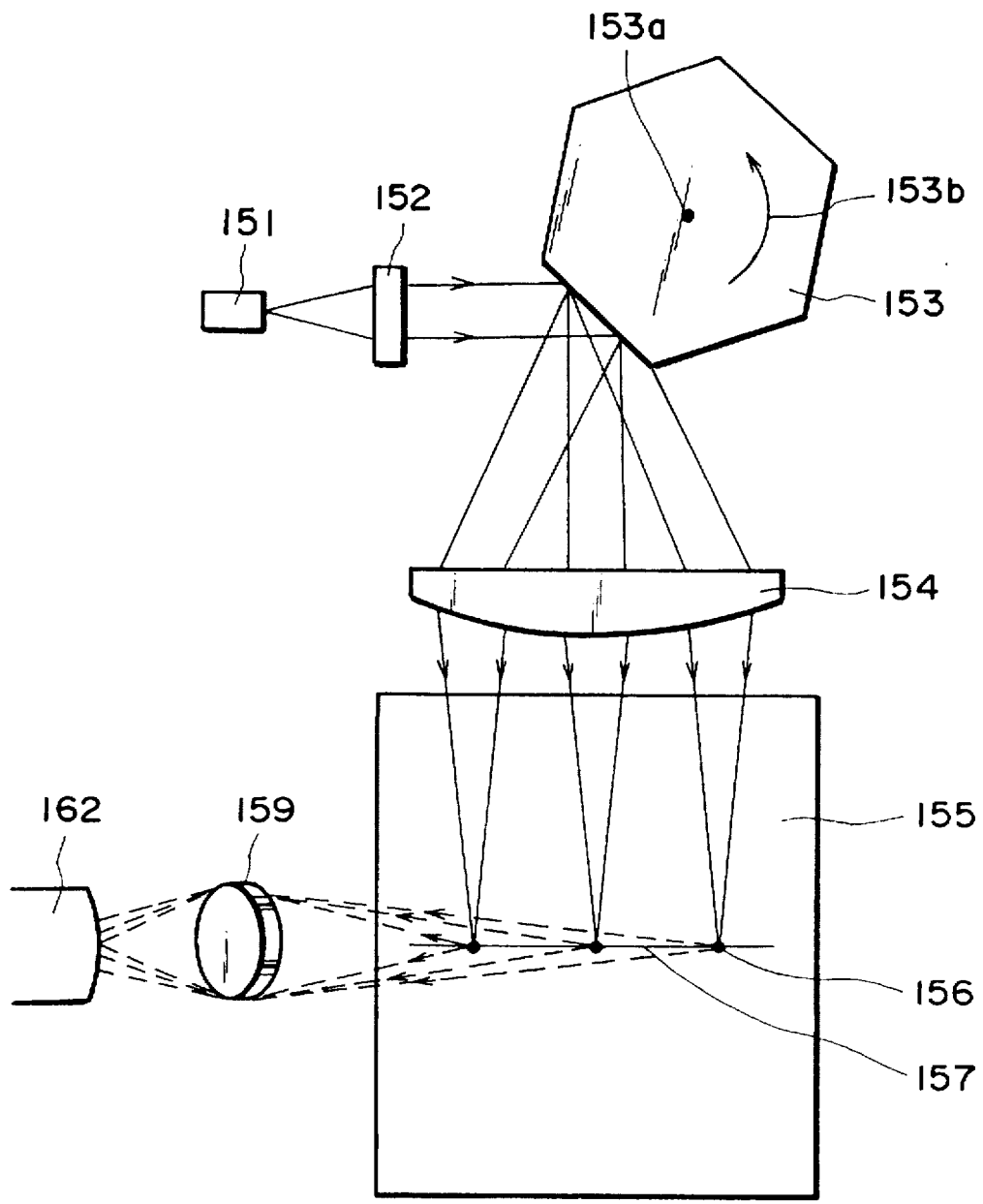
FIG. 17 is a schematic view of a main portion of another known type particle inspection system.
Figure 18:
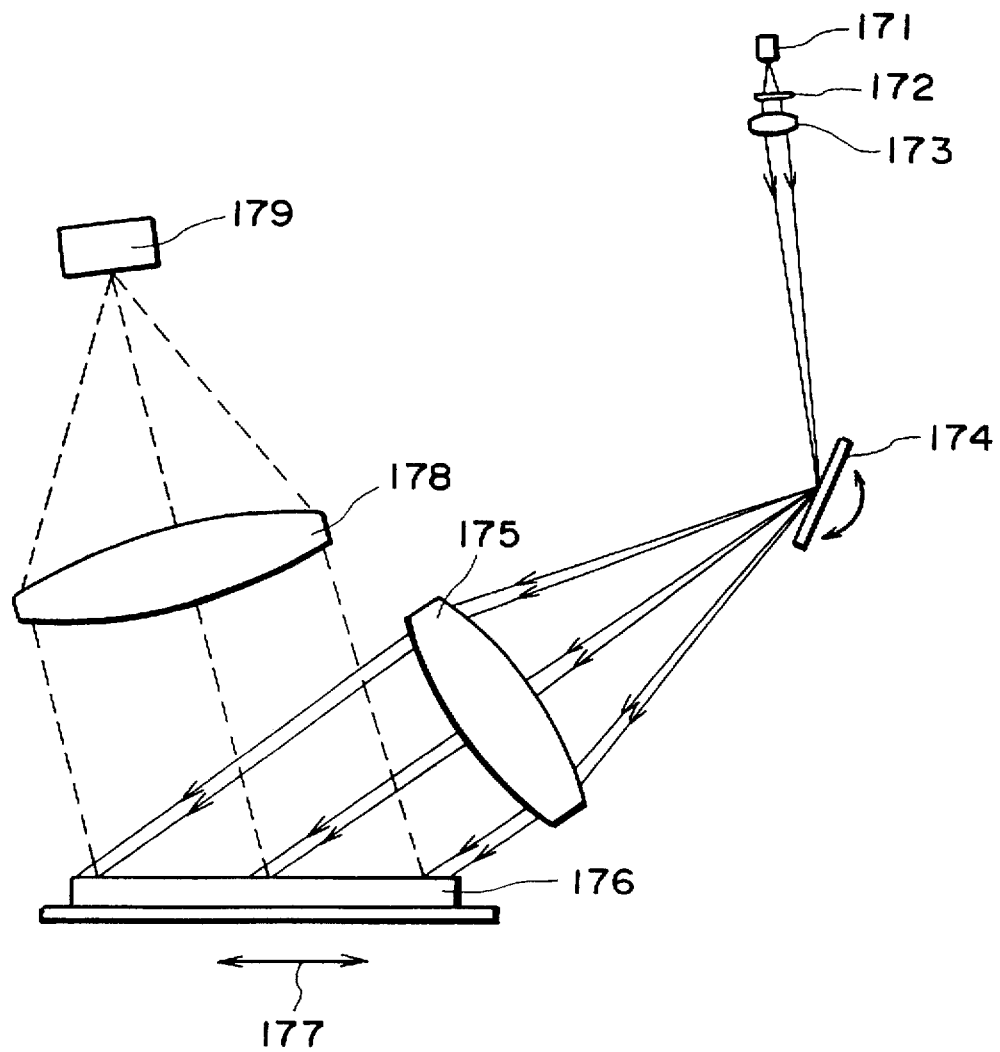
FIG. 18 is a schematic view of a main portion of a further known type particle inspection system.

In this embodiment, a diffusion plate 38 is disposed at a position corresponding to the surface to be inspected, in the inspection system example of FIG. 16, and a light spot as formed on the diffusion plate 38 serves as a secondary light source. Through a projection lens 39 of a similar structure as that of the projection lens 29 of FIG. 11, the surface 6 to be inspected is optically scanned. The structure of the remaining portion is essentially the same as the preceding embodiment.

In the drawing, a laser beam emitted by a laser light source 34 passes a beam expander 35 by which its beam diameter is expanded. The expanded laser beam then impinges on the reflection surface of a polygonal mirror 36. The laser beam as reflected by this reflection surface is influenced by a converging function of an f-θ lens 37, by which it is imaged as a light spot upon the diffusion plate 38 disposed on the image plane of the f-θ lens 37. With the rotation of the polygonal mirror 36, the beam spot scanningly displaces along the diffusion plate 38. The beam diffused by the diffusion plate 38 is again collected by a projection lens 39 upon the imaging plane (surface 6 to be inspected). Thus, with the rotation of the polygonal mirror 36, the light spot scanningly displaces along the image plane 6 of the projection lens 39.

It is to be noted that the optical axis of the f-θ lens 37 has an inclination within the plane of scan, with respect to the optical axis of the projection lens 39. Therefore, within the scan plane, the scan direction 5 has an inclination with respect to a direction perpendicular to the optical axis of the projection lens 39.

In this embodiment, as a scanning optical system before the diffusion plate 38, a conventional ordinary optical system is usable. Also, in this embodiment, in place of the diffusion plate 38, a diffraction grating or a hologram device may be used to diffract the beam toward the projection lens 39.

[Ninth Embodiment]

FIG. 14 is a block diagram of a main portion of an embodiment of a semiconductor device manufacturing method according to the present invention.

In this embodiment, the invention is applied to a manufacturing system for printing, on a wafer, a circuit pattern of an original such as a reticle or photomask, for manufacture of semiconductor devices. Generally, the manufacturing system includes an exposure apparatus, an original accommodating unit, an original inspecting unit and a controller, all being placed in a clean room.

In FIG. 14, denoted at 901 is a deep ultraviolet light source such as an excimer laser, and denoted at 902 is an illumination system of unit structure. These components serve to illuminate an original 903, placed at the exposure station EP, from above and with a predetermined N.A. (numerical number) at one time. Denoted at 909 is a projection lens for projecting and printing thereby a circuit pattern formed on the original 903 onto a wafer 910 such as a silicon substrate, for example. In a projection exposure process, an exposure operation is repeated while the wafer 910 is moved one shot by one shot in accordance with the step feeding of a movable stage 911. Denoted at 900 is an alignment system for aligning the original 903 and the wafer 910 with each other, before a start of the exposure operation. This alignment system includes at least one original observation microscope system.

The elements described above are components of the exposure apparatus.

Denoted at 914 is an original accommodating unit in which a plurality of originals are accommodated. Denoted at 913 is an inspecting system (particle inspection system) for detecting the presence or absence of a particle on an original. This inspecting system has a structure in accordance with any one of the embodiments described hereinbefore. As a particular one of the originals in the accommodating unit is selected and taken out thereof and before it is moved to and placed at the exposure station EP, particle inspection is carried out thereto by using the inspecting system 913.

The principle and operation of such particle inspection is in accordance with any one of the embodiments described hereinbefore. The controller 918 controls the sequence of the manufacturing system as a whole, and specifically it controls the operations of the accommodating unit 914 and the inspection system 913 as well as the alignment operation, the exposure operation and the wafer stepwise feeding operation which are basic operations of the exposure apparatus.

Semiconductor device manufacturing processes using the manufacturing system of this embodiment will now be explained.

First, an original 903 to be used is taken out from the accommodating unit 914, and it is introduced into the inspection system 913.

Then, by using this inspection system 913, particle inspection of the original 903 is carried out. If absence of a particle is confirmed, this original is moved to and placed at the exposure station EP. Subsequently, a semiconductor wafer 910 which is to be exposed is moved onto the movable stage 911. Then, through a step-and-repeat process, a pattern of the original is projected and printed in a reduced scale onto different regions on the semiconductor wafer 910 one shot by one shot in accordance with the stepwise motion of the movable stage 910. This operation is repeated.

Exposure of the whole surface of one semiconductor wafer 910 is completed, it is unloaded and a next wafer is loaded, and step-and-repeat exposures are made thereto to print the pattern of the original thereon.

Exposed wafers having been treated in the exposure process are then processed through a developing process and an etching process in a separate apparatus, different from this system. Thereafter, assembling operations such as a dicing operation, a wire bonding operation and a packaging operation are made whereby semiconductor devices are manufactured.

[Tenth embodiment]

Figure 15:
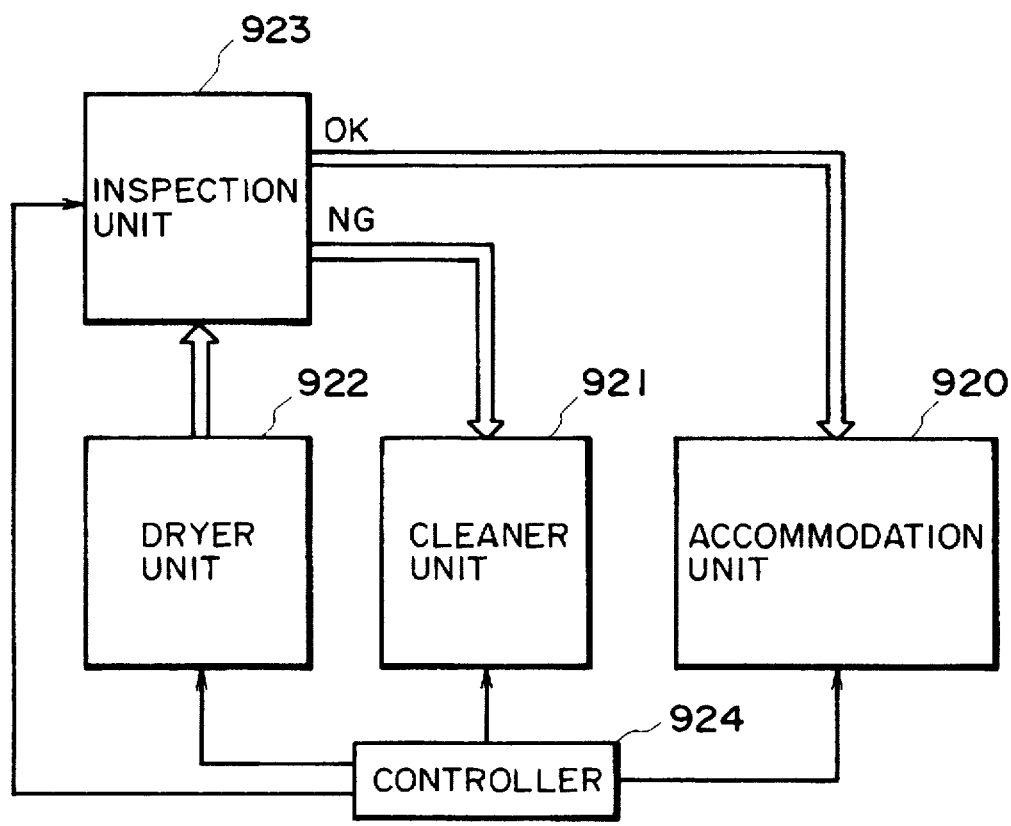
FIG. 15 is a block diagram of a main portion of a semiconductor device manufacturing method according to another embodiment of the present invention.

FIG. 15 is a block diagram of an embodiment of an original cleaning and inspecting system for the manufacture of semiconductor devices. Generally, this system comprises an original accommodating unit, a cleaning unit, a dryer unit, an inspection unit and a controller, all being placed in a clean chamber.

In FIG. 15, denoted at 920 is an original accommodating unit in which a plurality of originals are accommodated. An original to be cleaned is supplied therefrom. Denoted at 921 a cleaning unit for cleaning an original by using pure water. Denoted at 922 is a dryer unit for drying a cleaned original. Denoted at 923 is an original inspection unit having a structure according to any one of the embodiments described hereinbefore. It performs particle inspection of an original after being cleaned. Denoted at 924 is a controller for controlling the sequence of the system as a whole.

The operation will now be explained. First, an original to be cleaned is taken out of the original accommodating unit 920, and it is introduced into the cleaning unit 921. The original thus cleaned by the cleaning unit 921 is fed into the dryer unit 922, and it is dried. After it is dried, the original is introduced into the inspection unit 923 by which particle inspection of the original is performed in accordance with any one of the methods in the embodiments described hereinbefore.

Unless a particle is detected as a result of inspection, the original is moved back into the accommodating unit 920. If a particle is detected, the original is moved back into the cleaning unit 921 and it is cleaned again. After it is subsequently dried by the dryer unit 922, it is inspected again by the inspection unit 923. This operation is repeated until all particles are removed completely. Then, the thus cleaned original is moved back into the accommodating unit 920.

After this, a cleaned original is introduced into an exposure apparatus. Then, a circuit pattern of the original is printed on a semiconductor wafer, and semiconductor devices are manufactured.

While the invention has been described with reference to the structures disclosed herein, it is not confined to the details set forth and this application is intended to cover such modifications or changes as may come within the purposes of the improvements or the scope of the following claims.

What is claimed is:

1. An inspection system for inspecting a surface of an object, said system comprising:
   a light source;
   a scanning lens system for linearly scanning the surface with light from said light source, said scanning lens system having an asymmetrical refracting power in a direction of the scan, for providing a convergent light beam, to be focused on the surface to image a spot on the surface at a focal distance which is changeable in accordance with the position of scan on the surface; and
   a detector for receiving light from the surface.

2. A system according to claim 1, wherein said scanning lens system further comprises a scanning mirror and further comprising a lens having a shape asymmetrical with respect to an optical axis.

3. A system according to claim 1, wherein said scanning lens system further comprises a scanning mirror and further comprising a hologram member having a changing grating pitch.

4. A system according to claim 1, wherein said scanning lens system further comprises a scanning mirror and a lens movable along an optical axis for directing the light from said light source to said scanning mirror.

5. A system according to claim 1, wherein said scanning lens system further comprises deflecting means for reflectively deflecting received light in different directions with different refractivities.

6. A device manufacturing method usable with a reticle having a device pattern, said method comprising the steps of:
   scanning a surface of the reticle to be inspected, with light from a light source and through a scanning lens system having an asymmetrical refracting power in a direction of the scan, wherein the scanning lens system provides a convergent light beam being focused on the surface to image a spot on the surface at a focal distance which is changeable in accordance with the position of scan on the surface;
   receiving, through light receiving means, scattered light from the surface and performing inspection of the reticle on the basis of the result of the light reception; and
   transferring the device pattern of the inspected reticle to a substrate through a lithographic process.

7. An inspection method for inspecting a surface of an object, said method comprising the steps of:
   providing a light beam;
   deflecting the light beam to perform a linear scan of the surface;
   causing the light beam to be focused on the surface to image a spot on the surface at a focal distance which is changeable in accordance with the position of scan on the surface, by use of a scanning lens system having an asymmetrical refracting power in the direction of the scan; and
   detecting light from the surface.

* * * * *

UNITED STATES PATENT AND TRADEMARK OFFICE
CERTIFICATE OF CORRECTION

PATENT NO. : 5,767,962

DATED : June 16, 1998

INVENTORS : MASAYUKI SUZUKI, ET AL.

It is certified that error appears in the above-identified patent and that said Letters Patent is hereby corrected as shown below:

COLUMN 1:

```
line 21, "the a" should read --a--;
line 22, "use" should read --the use--; and
line 30, "particle" should read --particles--.
```

COLUMN 2:

```
line 21, "178," should read --179,--; and
line 23, "178." should read --179.--.
```

COLUMN 6:

```
line 6, "a before" should read --before a--.
```

COLUMN 8:

```
line 2, "bean" should read --beam--.
```

UNITED STATES PATENT AND TRADEMARK OFFICE
CERTIFICATE OF CORRECTION

PATENT NO. : 5,767,962

DATED : June 16, 1998

INVENTORS : MASAYUKI SUZUKI, ET AL.

It is certified that error appears in the above-identified patent and that said Letters Patent is hereby corrected as shown below:

COLUMN 9:

line 44, "921" should read --921 is--.

Signed and Sealed this

Ninth Day of March, 1999

Attest:

Q. TODD DICKINSON

Attesting Officer

Acting Commissioner of Patents and Trademarks